United States Patent
Cook

Patent Number: 6,083,242
Date of Patent: Jul. 4, 2000

[54] SURGICAL STAPLES WITH DEFORMATION ZONES OF NON-UNIFORM CROSS SECTION

[75] Inventor: Melvin S. Cook, Hohokus, N.J.

[73] Assignee: Holobeam, Inc., Hohokus, N.J.

[21] Appl. No.: 09/251,450

[22] Filed: Feb. 17, 1999

[51] Int. Cl.[7] .................................................... A61B 17/08

[52] U.S. Cl. ............................................................ 606/219

[58] Field of Search .............................. 606/75, 151, 157, 606/158, 219, 220, 221; 411/451, 460, 920

[56] References Cited

U.S. PATENT DOCUMENTS

| | | |
|---|---|---|
| 5,445,648 | 8/1995 | Cook ........................................ 606/219 |
| 5,814,763 | 9/1998 | Kirma ................................. 174/44 CC |

Primary Examiner—Michael Buiz
Assistant Examiner—Vy Q. Bui
Attorney, Agent, or Firm—Kaplan & Gilman, LLP

[57] ABSTRACT

An improved staple for use in internal surgery is disclosed. This improved staple has a deformation zone in each leg that varies in cross section along the length of the deformation zone. These cross sections are shaped so as to control staple leg deformation during staple installation into tissue in order to more effectively produce hemostasis and unite tissues and minimize tissue damage.

5 Claims, 1 Drawing Sheet

SURGICAL STAPLES WITH DEFORMATION ZONES OF NON-UNIFORM CROSS SECTION

TECHNICAL FIELD

This invention relates to improved staples for use in internal surgery, and more particularly to surgical staples having a deformation zone in each leg that varies in cross section along its length in such a manner as to more effectively produce hemostasis and unite tissues and minimize tissue damage.

BACKGROUND OF THE INVENTION

The present invention relates to surgical staples with two legs and a back span (crown) and at least one deformation zone in each leg to control staple deformation during installation for producing hemostasis, uniting tissues and minimizing tissue damage. In internal surgery, deformed staples must develop sufficient tissue compression to achieve hemostasis but should not so develop so much compression that excessive tissue damage results. Insufficient compression results in leakages and excessive compression results in excessive tissue damage. Tissue damage can lead to tissue necrosis, and tissue necrosis results in scar tissue and may also result in leakage. Scar tissue shrinks over time, and tissue shrinkage may require additional medical attention. Leakages may also require additional medical attention and may lead to mortality.

Several patents have issued to the Assignee of the present invention and an additional patent application has been filed, all of which disclose solutions to the aforementioned problems. These include U.S. Pat. Nos. 5,445,648; 5,667,527; 5,342,396, 5,749,896 and 09/020,162. These patents and the patent application cited above all relate to surgical staples for use in internal surgery which incorporate deformation zones, i.e., regions formed in the legs which tend to bend and deform more easily than adjacent regions of the legs when the staple is installed into tissue in order to more effectively produce tissue compression, unit tissues and minimize tissue damage. In the above-cited patents and patent applications, the intermediate regions of the deformation zones, i.e., the regions intermediate the end regions of the deformation zones, have a substantially uniform cross section. Such a substantially uniform cross section means that the disclosed staple do not adjust to tissue thickness as much as would be desirable to most effectively produce hemostasis and minimize tissue damage.

Although the staple leg deformation zones disclosed in the aforementioned patents and patent application represent a significant improvement over the prior art, farther improvement is possible if the cross sections of the intermediate regions of the deformation zones are varied along their length in such a manner as to optimize the shapes of the deformed installed staples since this controls tissue compression and affects tissue damage.

It is a purpose of the present invention to produce staples having deformation zones that vary in cross section along their intermediate regions in order that the staple can adjust to tissue thickness and density during its deformation so as to optimize tissue compression and to minimize tissue damage.

It is an additional purpose of the present invention to produce staples having deformation zones that vary in cross section along their intermediate regions so that the legs in the deformation zones so as to optimize tissue compression and to minimize tissue damage.

SUMMARY OF THE INVENTION

The improvement over the prior art achieved by the present invention helps in producing more effective hemostasis and in minimizing tissue necrosis. A deformation zone typically has an end region at each end of the deformation zone. In these end regions, the cross section of the leg changes rapidly. A deformation zone also has a region intermediate to these two end regions where in the prior art the cross section was uniform. The change in cross section from the leg region located immediately outside a deformation zone and the changes in cross section along the end region of the deformation zone leads to stress concentration that tends to produce more bending in the portions of the intermediate regions of the deformation zones immediately adjacent these end regions than in the remainder of the intermediate regions of the deformation zones during deformation of the staple leg as the staple is pushed against the stapler anvil when the leg cross section in the intermediate region is constant. The improvement of the present invention over the prior art is achieved by varying the cross section of the intermediate regions of the deformation zones so that they bend uniformly along the length of these intermediate regions when the staple leg is deformed during staple installation into tissue. The desirable varying of the cross section is achieved by shaping, e.g., tapering or curving, the cross sections of the intermediate regions of the deformation zones so as to result in uniform bending when the staple leg is bent and deformed. When bending is evenly distributed over the length of the deformation zones, this uniform bending helps in obtaining hemostasis and in minimizing tissue necrosis and allows the staple to respond to varying tissue thickness by deforming such that a smaller area is enclosed by the staple when the enclosed tissue is thin than is enclosed by the staple when the enclosed tissue is thick. It further is beneficial in producing a stronger deformed staple and thus producing stronger tissue unions when bending is more uniformly distributed along the length of the deformation zone.

DESCRIPTIONS OF THE PREFERRED EMBODIMENTS

Figure 1:
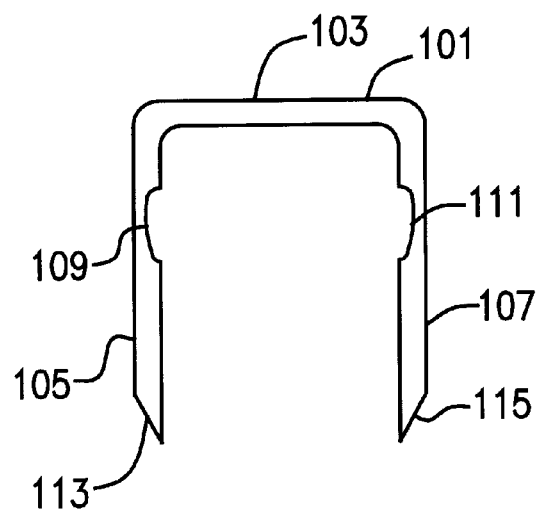
FIG. 1 shows a side view of an exemplary staple incorporating the present invention.

FIG. 1 shows staple 101 including back span (crown) 103 and legs 105 and 107. Leg 105 includes deformation zone 109 and point 113. Leg 107 includes deformation zone 111 and point 115.

Figure 2:
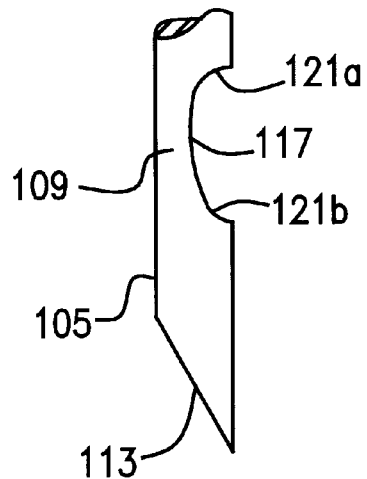
FIG. 2 shows an exploded view of a side view of a first deformation zone formed in accordance with the teaching of the present invention.

In FIGS. 2, we show intermediate portion 117 of deformation zone 109 located between the end portions 121a and 121b of staple 101 shown in FIG. 1. The cross section of the intermediate portion 117 is shaped such that the middle of the intermediate portion 117 is thinner than the portions of the intermediate zone closest to the end regions 121a and 121b. Typically, a deformation zone is produced by striking the wire, e.g., the titanium or stainless steel wire, used in forming the staple so that material is not removed while the cross section is modified. Therefore, while in the side view of the deformation zone shown in FIG. 2 is thinnest at the middle of the deformation zone, the width of the cross section orthogonal to this view, i.e., viewed along the direction of the back span, the material is widest. Since there is stress concentration caused by the transition in leg cross section at the end regions of the deformation zones, this helps to distribute the bending stresses so that more uniform bending occurs when the legs impinge against the anvil of the stapler pushing the staple than would be the case if there were a constant cross section through the intermediate portions of the deformation zones.

Figure 3:
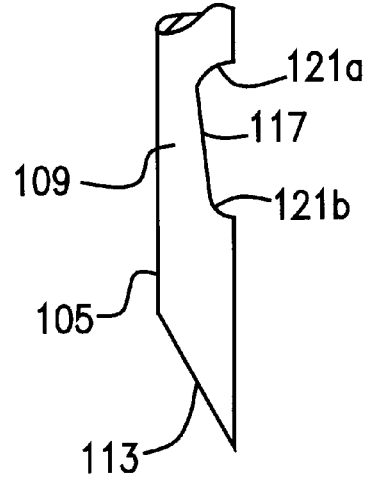
FIG. 3 shows an exploded view of a side view of a second deformation zone formed in accordance with the teaching of the present invention.

In FIG. 3, the cross section of the intermediate portion 117 of the deformation zone varies along its length and is thickest at its end closest to end region 121a and thickest at end region 121b, i.e., there is a taper which typically is six degrees or less along the intermediate region of the deformation zone. Since there is stress concentration caused by the transition in leg cross section at the end regions of the deformation zones, this helps to distribute the bending stresses so that more uniform bending occurs than would be the case if there were a constant cross section through the intermediate portion when the ends of the staple legs stroke the stapler anvil when pushed by the stapler than would be the case if the cross section were uniform through the intermediate regions of the deformation zones.

When a staple is installed by being pushed by a stapler, the staple legs start to bend after their tips impinge against the stapler anvil. There is stress concentration in the deformation zones immediately adjacent to the end portions, and if the deformation zones are not shaped so as to produce a uniform bending along their intermediate portions, bending will initially occur somewhat preferentially near the end portions. In the present invention, the intermediate regions are so shaped to weaken their resistance to leg bending so that more uniform bending occurs along the length of the intermediate regions during staple deformation. This shaping results in better control of the configuration assumed by the deformed staple than if such shaping were absent.

In the present invention, the configuration of the deformed staple responds to the thickness of the tissues being stapled since tissue thickness affects stress distribution in the deformation zones. The invented staple deforms such that the deformed staple has a more generally rectangular configuration with straighter legs when the tissue are thinner than when the tissues are thicker. This gives better control of tissue compression than is possible if the staple deformation does not respond to the combination of tissue thickness and density.

While the above describes the preferred embodiment of the present invention and a second embodiment of the present invention, modifications, variations and additions of the invention will be obvious to those skilled in the art. All such modifications, variations and additions of the invention are intended to be covered by the following claims.

What is claimed is:

1. A staple having a backspan and two legs, each of said legs having a tip and an elongated deformation zone, each of said deformation zones being more susceptible to bending than other regions of staple legs adjacent to each of said deformation zones when said tips of such staple legs are forced toward each other, the legs having a cross section area outside the deformation zones, each of said elongated deformation zones including an intermediate region that is tapered and that varies in cross sectional area within said deformation zone, along the length thereof, such that said cross sectional area is different at a location of said region closest to said backspan than it is at a location of said region closest to said tip of said legs, the cross section within said deformation zone smoothly varying at each end thereof until matching the cross section of said legs outside the deformation zone.

2. The staple of claim 1 wherein said intermediate regions vary in cross sectional area at a constant rate, and wherein said constant rate is linear.

3. The staple of claim 2 wherein said constant rate is no more than six degrees.

4. A staple having a back span and two legs, each of said legs having a tip, each leg having an elongated deformation zone, said deformation zones being more susceptible to bending than other regions of said staple legs adjacent to said deformation zones when said tips of said legs are forced toward each other, each of said deformation zones having a length, a width, and a depth, wherein both the width and the depth of the deformation zones vary along the length thereof, and wherein the depth is thinner toward the center of each of said elongated deformation zones than at either end thereof.

5. The staple of claim 4 wherein the depth and width vary such that as the depth increases, the width decreases and as the width decreases, the depth increases.

* * * * *